United States Patent [19]

Hayashi et al.

[11] Patent Number: 4,971,901
[45] Date of Patent: Nov. 20, 1990

[54] PROCESS FOR PREPARING ENZYME ELECTRODES

[75] Inventors: Ryuzo Hayashi, Higashiosaka; Akio Kariyone, Kyoto, both of Japan

[73] Assignee: Kanzaki Paper Manufacturing Co., Ltd., Tokyo, Japan

[21] Appl. No.: 146,202

[22] Filed: Jan. 20, 1988

[30] Foreign Application Priority Data

Jan. 24, 1987 [JP] Japan .................... 62-14648

[51] Int. Cl.$^5$ .............. C12N 11/14; C12N 11/02; C12M 1/40; G01N 27/26
[52] U.S. Cl. ................... 435/176; 204/403; 435/14; 435/25; 435/177; 435/288; 435/817
[58] Field of Search ............ 435/176, 177, 288, 817, 435/14, 25; 204/403

[56] References Cited

U.S. PATENT DOCUMENTS

| | | | |
|---|---|---|---|
| 4,229,536 | 10/1980 | DeFilippi | 435/176 |
| 4,266,029 | 5/1981 | Branner-Jorgensen | 435/176 |
| 4,464,468 | 8/1984 | Avrameas et al. | 435/177 |
| 4,476,005 | 10/1984 | Tokinaga et al. | 435/817 X |
| 4,795,707 | 1/1989 | Niiyama et al. | 435/817 X |
| 4,833,075 | 5/1989 | Vijayalakshmi et al. | 435/177 X |

OTHER PUBLICATIONS

Vadgama, P., J. Med. Eng. & Technol., vol. 5, No. 6, 1981, pp. 293–298.

*Primary Examiner*—David M. Naff
*Attorney, Agent, or Firm*—Wenderoth, Lind & Ponack

[57] ABSTRACT

An enzyme electrode is prepared by a process wherein an albumin solution containing 0.05 to 0.5% by weight of a multifunctional aldehyde is applied onto the surface of an electroconductive substrate while maintaining the atmospheric temperature at 0° to 20° C. to thereby form a crosslinked albumin layer on the surface of the electroconductive substrate. Thereafter a solution containing 0.5% by weight or less of a multifunctional aldehyde and a predetermined amount of an oxidase capable of producing hydrogen peroxide ($H_2O_2$) is applied on the surface of the previously formed crosslinked albumin layer to form a $H_2O_2$ productive oxidase containing layer.

15 Claims, No Drawings

PROCESS FOR PREPARING ENZYME ELECTRODES

FIELD OF THE INVENTION

This invention relates to a process for preparing an emzyme immobilized electrode (hereinafter referred to as "enzyme electrode"). More particularly, it relates to a process for preparing an improved enzyme electrode which is free from influences of electrochemically interfering substances and which excels in the response sensitivity and response speed.

BACKGROUND OF THE INVENTION

Quantitative determination of unknown substances contained in biological materials and foods utilizing an enzymatic reaction has been widely practiced since there are various advantages for the enzymatic reaction that it is high speed in response and it has a substrate specificity.

And in recent years, the public attention has been focused on enzymatic quantitative determination methods using an enzyme electrode not only in the medical field but also in the food and drug fields since there are advantages that the use of an enzyme in a small amount makes it possible to practice microanalysis of a trace substance contained in a biological material, food, drug or the like. In addition to this, the enzyme can be repeatedly used.

For instance, among such enzymatic quantitative determination methods, there is known the so-called amperometric method of measuring an electric current in the electrode reaction of a material produced or consumed by an enzymatic reaction by applying a constant voltage on the enzymatic electrode. And, the amperometric method has been generally evaluated as being the most preferred since there are various advantages that the constitution of the electrodes to be used is simple, the electrode may be easily made highly sensitive, and in the case of the electrode utilizing the enzymatic reaction of an oxidase producing hydrogen peroxide, it is excellent in response speed and sensitivity.

However, there still remain an unsolved problem for said amperometic method that in the case where a sample to be examined contains a reducing substance, such reducing substance often renders it incapable of precisely determining the content of an objective substance to be observed.

For instance, the mechanism of quantitatively determining the glucose content in a sample using glucose-oxidase (GOD) is based on the following reactions:

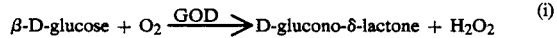

(i)

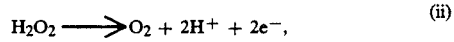

(ii)

wherein hydrogen peroxide produced in the reaction (i) will cause an electrode reaction of the above reaction formula (ii) with the application of a voltage of about +0.6 V vs a saturated calomel electrode (hereinafter referred to as "SCE") where an electric current which is caused at that time is relative to the glucose content in the sample. Because of this, the quantitative determination of the glucose content becomes possible.

In this system, there is a high substrate specificity against the glucose to be determined in the enzymatic reaction (i). However, in the electrode reaction (ii), various reducing materials, i.e., interfering materials contained in the sample, are oxidized on the electrode to cause an extra electric current, which will be measured together with the electric current based on the glucose. Because of this, it becomes impossible to obtain an accurate value for the glucose content. As such interfering material present in foods or biological fluids, there are known ascorbic acid, urea, reduced glutathione, thyrosin, etc.

In order to solve the above problem, there has been made a proposal of providing a permselective membrane consisting of acetylcellulose or the like between the enzyme immobilized layer and the electroconductive substrate made of platinum, etc. in the system of measuring the amount of hydrogen peroxide produced as a result of the oxidase reaction in a way that the measurement can be carried out under the condition of allowing the selective permeation of the hydrogen peroxide.

Even for this proposal, there is a problem that since there exists a clearance filled with an electrolyte solution, buffer solution or the like between the permselective membrane - enzyme layer complex system and the electroconductive substrate, it takes some period of time for the resulting hydrogen peroxide to be diffused in the permselective membrane and the clearance, and because of this, the response speed will be delayed. In addition to this, there is another problem that because the resulting hydrogen peroxide is diluted within the clearance, it is necessitated to highten the sensitivity of the electric detecting circuits.

There has been made an attempt to make the permselective membrane thinner in order to eliminate the above problems. However, such attempt is not effective because the foregoing interfering materials partly become permeated in this case.

There has been made a further attempt to make the scale of the electrode smaller, that is, to be a microelectrode, in order to prevent the response speed from being delayed due to the foregoing diffusion or/and the foregoing dilution of the resulting hydrogen peroxide. However this attempt is not practical because there are problems in the case of such microelectrode that the current density will become smaller as the electrode surface area diminishes in size and as a result, the electric circuit becomes necessary to have a high sensitivity.

There has been made a still further attempt to dispose the foregoing permselective membrane directly on the surface of the electroconductive substrate by means of the casting technique. However, for the electrode system prepared under this attempt, there is a problem that the adhesion between the foregoing permselective membrane and the electroconductive substrate is not strong enough and its durability is not satisfactory. This problem becomes significant especially in the case of developing an automatic and high speed flow-type enzyme-based analyzer since there will be given a specific shearing force based on the liquid flow onto the permselective membrane.

SUMMARY OF THE INVENTION

The present inventors have conducted extensive studies in order to solve the problems in the aforementioned known enzyme electrode and in order to develop a new process for effectively and easily preparing a desirable enzyme electrode which is free from the foregoing problems.

As a result, the present inventors have finally found a process which enables efficient and stable preparation of a desirable improved enzyme electrode which does not receive such undesired influences of the interfering materials as found on the known enzyme electrode and which has a wealth of many practically applicable characteristics required therefor. The process is carried out by firstly forming a crosslinked albumin layer on an electroconductive substrate under a specific condition then forming an enzyme layer on the previously formed crosslinked albumin layer.

It is therefore an object of this invention to provide an improved enzyme electrode which is free from the problems due to the influences of the interfering materials which are found on the known enzyme electrode, which excels in the sensitivity, response speed and durability, and which is not deteriorated upon repeated use over a long period of time.

Another object of this invention is to provide a process for preparing the above enzyme electrode. characterized in that an albumin solution containing 0.05 to 0.5% by weight of a multifunctional aldehyde is applied onto the surface of an electroconductive substrate while maintaining the atmospheric temperature at 0 to 20° C. to thereby form a crosslinked albumin layer on the surface of the electroconductive substrate and successively a solution containing 0.5% by weight or less of a multifunctional aldehyde and a predetermined amount of an oxidase capable of producing hydrogen peroxide ($H_2O_2$) is applied on the surface of the previously formed crosslinked albumin layer to form a $H_2O_2$ productive oxidase containing layer (hereinafter referred to as "$H_2O_2$ productive layer").

DESCRIPTION OF THE PREFERRED EMBODIMENT

The electroconductive substrate to be used in this invention may be one that is made of an inorganic material such as platinum, graphite, etc.. Among these materials, platinum is the most desirable from the viewpoint that platinum is highly sensitive to $H_2O_2$ and it has a desired function to show the marked limiting current.

The shape of the electroconductive substrate may be optionally determined. Examples are bar, plate and suitable like shapes.

The surface of the electroconductive substrate on which a crosslinked albumin layer is to be formed is desired to be in such a state that does not cause unevenness in the sensitivity for the resulting enzyme electrode.

In a preferred embodiment in this respect, the surface of the electroconductive substrate is firstly polished with an emery paper or powdery alumina then subjected to ultrasonic cleaning to remove the extraneous matter from the polished surface, thereby obtaining the electroconductive substrate having a desired clean surface.

In an alternative, after being polished in the way as above mentioned, the surface-polished electroconductive substrate is scanned with triangular wave potential sweep in an aqueous solution of dilute sulfuric acid and air-dried to thereby obtain an electroconductive substrate having a desired clean surface.

On the thus treated clean surface of the electroconductive substrate, there are formed a crosslinked albumin layer then a $H_2O_2$ productive layer.

As the starting raw material albumin to be used for the formation of said crosslinked albumin layer, there can be illustrated human serum albumin, egg-white albumin, bovine serum albumin, etc.. Among these albumins, bovine serum albumin is the most preferred since it is commercially provided in a functionally stable state and with a relatively inexpensive cost.

The formation of an objective crosslinked albumin layer using such albumin may be carried out without using any coupling reagent. However, there may be formed a more desirable objective crosslinked albumin layer in the case of using an appropriate coupling reagent such as a silane coupling reagent. That is, in the latter case, the adhesion of the resulting crosslinked albumin layer to the surface of the electroconductive substrate is desirably strengthened and a result, the enzyme electrode obtained is such that it enables one to stably and repeatedly measure the accurate content of an objective material in a sample for a long period of time.

Usable as such coupling reagents are, for example, $\gamma$-aminopropyltriethoxy silane, 4-aminobutyldimethylmethoxy silane, 4-aminobutyltriethoxy silane, etc. and among these silane coupling reagents, $\gamma$-aminopropyltriethoxy silane are the most preferred because of its excellent bonding capability to platinum.

In a preferred embodiment of the process for preparing the enzyme electrode according to this invention, prior to forming said crosslinked albumin layer on the foregoing surface-cleaned electroconductive substrate, the electroconductive substrate is treated with the foregoing coupling reagent.

In a further preferred embodiment in this respect, prior to subjecting the surface-cleaned electroconductive platinum substrate to said coupling reagent treatment, it is desired to form a thin oxide coating on the cleaned surface of the electroconductive platinum substrate by subjecting it to the above electrolytic treatment under a specific condition to allow the formation of said oxide coat.

In the latter case, there are advantages that there may be obtained a desired enzyme electrode of which layer comprised of a permselective crosslinked albumin layer and a $H_2O_2$ productive layer are firmly adhered to the surface of the electroconductive substrate and which is particularly excellent in durability. And, even in the case of preparing a great many enzyme electrodes, there may be obtained the desired enzyme electrodes of an uniform quality which do not have any unevenness in the output current values.

In a preferred embodiment of the above electrolytic treatment with a specific electric potential for the foregoing surface-cleaned electroconductive substrate, it is carried out by maintaining the substrate as the working electrode in a 0.05 to 0.5 M dilute sulfuric acid at an electric potential of preferably +1.0 to +1.5 V or more preferably +1.2 to 1.4 V vs Ag/AgCl electrode for a period of preferably more than 30 seconds or more preferably more than 5 minutes. This treatment is more effective in the case where the substrate is of platinum because there is formed a thin surface coat comprised of $PtO_x$ layer containing hydroxy groups (hereinafter referred as "$PtO_x$ layer") and having a desirable uniform thickness.

In this case, when the treatment period is less than 30 seconds, said $PtO_x$ layer is slightly formed. When it exceeds 2 hours, there is formed such $PtO_x$ laYer that has an excessively large thickness to bring about impermissible reduction in the sensitivity for the resulting enzyme electrode.

The confirmation of the situation for said $PtO_x$ layer to have been formed on the electroconductive substrate by the above electrolytic treatment may be conducted in accordance with cyclic voltammetry.

That is, for the substrate for which the above electrolytic treatment has been made, a cyclic voltamgram is recorded in the direction of minus electric potential starting from +0.9 V at a sweep rate of about 1 V/sec. in 0.1 M sulfuric acid. In the case where a $PtO_x$ layer has been formed on the substrate, there will appear a reduction peak corresponding to said layer.

Now, as for the surface-treated electroconductive substrate for which the above electrolytic treatment has been made in this invention, there appear reduction peaks of around the same size on the resultant cyclic voltamgram and as a result, it is confirmed that there has been formed a $PtO_x$ layer of even thickness on the substrate. This PtOx layer is reproducible. In fact, even in the case where a plurality of the surface-cleaned electroconductive substrates are subjected to the above electrolytic treatment under the same condition, there is formed such desired $PtO_x$ layer in an uniform state on each of them.

On the other hand, there is not observed any such reduction peak for the surface-cleaned electroconductive substrate for which the above electrolytic treatment has not been made.

In addition, in the case where the above electrolytic treatment is carried out at an electric potential of more than +1.5 V vs Ag/AgCl electrode for a plurality of the surface-cleaned electroconductive, the enzyme electrodes prepared using the resultant substrates become such that they respectively give different reduction peaks on the cyclic voltamgram. And, the respective enzyme electrodes also become such that they respectively give different output values.

Further, in the case where the above electrolytic treatment is carried out at an electric potential of less than +1.0 V vs Ag/AgCl electrode, the oxidation reaction to cause the formation of the $PtO_x$ layer does not sufficiently occur on the surface-cleaned electroconductive substrate and as a result, it becomes difficult to very firmly connect a permselective crosslinked albumin layer and a $H_2O_2$ productive layer on the substrate.

In the most preferred embodiment of the process for preparing the enzyme electrode according to this invention, the surface-cleaned electroconductive substrate, on the surface of which a thin surface coat comprised by a $PtO_x$ layer has been formed, is immersed in a solution containing the foregoing silane coupling reagent to make the $PtO_x$ layer constituting the surface coat to have "Pt-O-Si" bonds. In this case, as the solution containing the foregoing silane coupling reagent, there can be illustrated a solution containing the foregoing silane coupling reagent in an organic solvent such as an anhydrous benzene solution and a toluene solution. As for the immersion period of said substrate in such organic solution, it is properly determined depending upon the amount and/or the kind of the foregoing silane coupling reagent to be used. However, it is preferably about 30 minutes.

In the case where the thus treated electroconductive substrate is used, the crosslinked albumin layer becomes very effectively formed in a firmly adhered state on the surface of the substrate. And even in the case where a plurality of enzyme electrodes are produced, every resulting enzyme electrode becomes such that it enables accurate measurement of an objective material contained in a sample without giving a practically unacceptable unevenness in the output values even upon repeated measurements for a long period of time.

The formation of a crosslinked albumin layer on an electroconductive substrate in this invention is carried out in the following way.

That is, there is prepared a solution containing a predetermined amount of one of the foregoing albumins in distilled water. Then, a predetermined amount of a multifunctional aldehyde is added to said solution to thereby obtain a coat-forming solution. The thus obtained solution is applied onto the surface of the electroconductive substrate by way of a known coating method to form a coat comprised of the solution and it is subjected to a crosslinking reaction under a specific condition to thereby form an objective permselective crosslinked albumin layer.

The concentration of the albumin to be contained in the coat-forming solution is properly determined having due particularly to the point that the albumin will be spread uniformly on the surface of the electroconductive substrate to form a permselective crosslinked albumin layer with an amount of 5 to 50 $g/m^2$ thereon. In view of this, it is desired to be controlled to 0.1 to 5% by weight.

And, in the case of preparing the above solution containing the albumin, the use of a saline buffer solution shall be avoided even in the case where it is necessitated to control the PH value of the solvent for the albumin because there will be precipitated such undesired salts which will hinder the uniform formation of an objective crosslinked albumin layer. In that case, it is desired to use an appropriate compound capable of controlling the PH value of the solvent (distilled water) such as acetic acid ($CH_3COOH$) or ammonia ($NH_3$) which does not cause precipitation of any salt.

As for the concentration of the multifunctional aldehyde to be contained in the coat-forming solution, when it is excessively high, the resulting crosslinked albumin layer becomes such that it does not exhibit sufficient permselective functions and allows the permeation of some interfering materials. On the other hand, when it is excessively low, the crosslinking reaction does not sufficiently occur within the layer constituent elements and as a result, the resulting albumin layer becomes such that is not sufficient in layer strength and cannot be repeatedly used for a long period of time.

In view of the above, the concentration of the multifunctional aldehyde to be contained in the coat-forming solution is preferably 0.05 to 0.5% by weight, and more preferably, 0.1 to 0.5% by weight.

Usable as the multifunctional aldehyde are, for example, glutaraldehyde, succinaldehyde, glyoxal, etc., and among these compounds, glutaraldehyde is the most preferred because it hardly hinders the activity of an enzyme.

In a preferred embodiment of forming an objective permselective crosslinked albumin layer on the surface of the electroconductive substrate using the foregoing coat-forming solution in this invention, said coat-forming solution is firstly applied onto the surface of the electroconductive substrate to form a coat comprised of the coat-forming solution thereon by way of a known coating method with a proper temperature, for example, room temperature, and which is then followed by the crosslinking reaction by maintaining at a temperature of preferably 0° C. to 20° C., more preferably 0° C. to 10° C., or most preferably 2° C. to 8° C. for a period of preferably 20 minutes to 24 hours or more preferably 30 minutes to 4 hours in an enclosed vessel to thereby cause the crosslinking reaction within said coat resulting in making said coat to be an objective permselective crosslinked albumin layer.

To maintain the coat-forming solution applied at a specific temperature in the above-mentioned range is an important factor in order to form the objective permselective crosslinked albumin layer according to this invention.

In fact, in the case where a plurality of the electroconductive substrates are coated with the foregoing coat-forming solution at room temperature and the resultant substrates are maintained at this temperature in order to cause the crosslinking reaction resulting in forming a permselective crosslinked albumin layer for each of the electroconductive substrates, although the crosslinking reaction proceeds for each electroconductive substrate, the resultant layers become such that they are uneven in their layer qualities and also are inferior and uneven in their permselective properties.

Further, even in the case where the above coat comprised of the foregoing coat-forming solution is maintained at the above-mentioned limited temperature, when the coat-forming solution applied is maintained for a longer period beyond the above-mentioned range, the resulting crosslinked albumin layer becomes such that it is insufficient in the permselective property.

In a preferred embodiment of obtaining a desired permselective crosslinked albumin layer, it is desired to purposely prevent the concentration of the multifunctional aldehyde in the coat-forming solution from being changed and in addition to this, to purposely prevent the coat-forming solution applied from being dried before it is sufficiently crosslinked during the process.

In attaining these purposes, it is effective to carry out the crosslinking reaction of the albumin with the multifunctional aldehyde in the coat comprised of the foregoing coat-forming solution in the following way. That is, the foregoing albumin containing solution is applied onto the surface of the electroconductive substrate to form a solution coat and the thus formed coat is maintained in a substantially enclosed vessel an atmosphere composed of multifunctional aldehyde saturated vapor of the above-mentioned limited temperature to cause said crosslinking reaction and to make said solution coat to be a permselective crosslinked albumin layer.

The formation of a $H_2O_2$ productive layer ($H_2O_2$ productive oxidase containing layer) on the thus formed permselective crosslinked albumin layer may be carried out successively soon after the formation of said crosslinked albumin layer has been completed.

However, in a preferred embodiment, prior to forming said $H_2O_2$ productive layer on the resultant crosslinked albumin layer, the electroconductive substrate having said crosslinked albumin layer thereon is taken out from the substantially enclosed vessel, and it is maintained at a temperature of 10° C. to 50° C. And, as for the period of maintaining said electroconductive substrate at this temperature, it is 15 to 30 minutes in the case where the temperature is 40° C.

By practicing the above process, not only the remaining excessive multifunctional aldehyde and moisture are removed from the resultant crosslinked albumin layer but also the crosslinking reaction is desirably completed and as a result, a desired permselective crosslinked albumin is formed.

In the process for preparaing the enzyme electrode according to this invention, there is formed a $H_2O_2$ productive layer ($H_2O_2$ productive oxidase containing layer) on the thus formed permselective crosslinked albumin layer using (i) an aqueous solution containing a $H_2O_2$ productive oxidase and a member selected from the above-mentioned multifunctional aldehydes or (ii) another aqueous solution containing other protein than said oxidase in addition to said two materials.

Usable as the $H_2O_2$ productive oxidase are, for example, glucose oxidase, galactose oxidase, alcohol oxidase and the like.

And, usable as said protein are, for example, gelatin, collagen, fibroin, albumin and the like.

The concentration of the $H_2O_2$ productive oxidase to be contained either in the above aqueous solution (i) or in the above aqueous solution (ii) is properly determined having due regard particularly to the point that the $H_2O_2$ productive oxidase will be spread uniformly on the surface of the previously formed permselective crosslinked albumin layer to form a $H_2O_2$ productive layer with an amount of 5 to 10g/$m^2$ thereon. In view of this, it is desired to be controlled to 0.1 to 5% by weight. Likewise, as for the concentration of said protein to be contained in the above aqueous solution (ii), it is desired to be controlled to 0.1 to 5% by weight.

In order to form the $H_2O_2$ productive layer on the surface of the previously formed permselective crosslinked albumin layer, one of the above-mentioned two solutions (i) and (ii) is applied onto the surface of said albumin layer so as to form a coat of uniform thickness in accordance with a known coating method. In the case of using the solution (ii), there are advantages that the physical strength of the resulting crosslinked enzymatic layer is fostered and the activity of the $H_2O_2$ productive oxidase may be stably maintained without being deactivated during the crosslinking reaction within the solution's coat on the previously formed permselective crosslinked albumin layer. And, as the protein to be used in this case, albumin is the most desirable in the viewpoint that the resulting $H_2O_2$ productive layer has good affinity with the permselective crosslinked albumin layer because both layers contain albumin as a common layer constituent. In either case of using the solution (i) or the solution (ii) for the formation of the $H_2O_2$ productive layer, the multifunctional aldehyde is likely to permeate into the previously formed permselective crosslinked albumin layer during the layer forming process.

Because of this, when the concentration of multfunctional aldehyde in the solution is high, the permselective property of the previously formed permselective crosslinked albumin layer will be diminished. In view of this, the concentration of the multifunctional aldehyde in the solution (i) or the solution (ii) is necessarily properly controlled within the limited range.

Specifically, it is preferably 0.5% by weight or less and more preferably, less than its concentration in the case of forming the permselective crosslinked albumin layer. However, in any case, it is necessary to be 0.1% by weight or more in view of immobilizing the $H_2O_2$ productive oxidase.

In the case of forming the $H_2O_2$ productive layer, it is possible to use a known buffer solution where necessary. In this case, its concentration is desired to be 0.1 mol/l or less in view of preventing the previously formed permselective crosslinked albumin layer from being damaged because of the buffer solution.

The formation of the H₂O₂ productive layer is carried out by maintaining the coat comprised of the above solution (i) or the above solution (ii) formed on the previously formed crosslinked albumin layer at about 40° C. for a period of 15 to 30 minutes, for example, in an incubator. And the immobilization of the $H_2O_2$ productive oxidase may be accomplished for a shorter period of time.

In accordance with the process according to this invention as above described, there may be effectively prepared a desired enzyme electrode having a permselective layer capable of selectively permeating only hydrogen peroxide but not any interfering materials. In addition to this advantage, there is brought about another significant advantage in accordance with the process according to this invention. Because there is formed such specific permselective layer directly on the electroconductive substrate, there may be effectively prepared such practically applicable and excellent enzyme electrode having an excellent durability, which does not cause any unnecessary dilution for the resulting hydrogen peroxide, which excels in the response sensitivity and the response speed, and which stably gives accurate output values without being deteriorated upon respected use for a long period of time.

PREFERRED EMBODIMENT OF THE INVENTION

The advantages of this invention are now described in more detail by reference to the following Examples, which are provided merely for illustrative purposes only, and are not intended to limit the scope of this invention.

EXAMPLE 1

In accordance with the procedures described below, a bar shaped enzyme electrode was prepared using a platinum wire of 2 mm in diameter as the electroconductive substrate.

The surface of the platinum wire was polished using an emery paper and powdery alumina of 0.5 μm in particle size. The resultant surface-polished platinum wire was immersed in a sulfuric acid aqueous solution of 0.1 mol/l and subjected to triangular wave potential sweep at an electric potential of −0.3 V to +1.3 V vs SCE and at a sweep rate of 1.0 V/sec. repeatedly for 5 minutes. Thereafter, the thus treated platinum wire was washed with distilled water, then air-dried at 40° C. for 15 minutes to thereby make the polished-surface of the platinum wire electrochemically clean.

The thus obtained platinum wire was vertically placed in an enclosed vessel in a way that its one top surface was horizontally situated. Then, 5 μl of an aqueous solution containing 2% by weight of bovine serum albumin (product of Sigma Co., Ltd.: Fraction V) and 0.2% by weight of glutaraldehyde was dropwise applied to the top surface of the platinum wire using a microcylinge to thereby form a coat comprised of said solution thereon. Thereafter, the platinum wire was transfered into another enclosed vessel of which the inner space was filled with saturated vapor generated from an aqueous solution of glutaraldehyde, and it was allowed to stand within said saturated vapor atmosphere at 4° C. for 2 hours. Successively, it was transfered into an incubator maintained at 40° C. and subjected to heat-treatment at this temperature for 30 minutes to thereby form a permselective crosslinked albumin layer on the polished-surface of the platinum wire.

After the platinum wire was cooled to about 15° C., 2.5 μl of an aqueous solution (PH value: about 7.0), prepared by adding glutaraldehyde in an amount to provide a content of 0.2% by weight in the aqueous solution to a 0.1 mol/l sodium phosphate buffer solution of 7.0 for PH value containing 1% by weight of glucose oxidase (product of Sigma Co., Ltd.: Type II, 36000 units/g) and 1% by weight of bovine serum albumin (product of Sigma Co., Ltd.: Fraction V), was dropwise applied onto the surface of the previously formed permselective crosslinked albumin layer to thereby form a coat comprised of said glucose oxidase containing solution on the previously formed albumin layer. Thereafter, the platinum wire was kept at 40° C. for 30 minutes, it was then washed with 0.1 mol/l sodium phosphate buffer solution (PH value: 7.0) and air-dried to thereby obtain an enzyme electrode.

The resultant enzyme electrode was set into the cell of a known flow injection apparatus and the electric potential to the counter electrode was adjusted to +0.6 V using a potentiostat. Then, a sodium phosphate buffer solution of PH 7.0 was allowed to flow at a flow rate of 1.0 ml/min., and at the same time, an amount of 10 μl for each of 10 mM hydrogen peroxide ($H_2O_2$), an aqueous solution of glucose, an aqueous solution of ascorbic acid was injected to the flow to measure the peak current value for each of these materials.

The results obtained were as shown in Table 1.

EXAMPLE 2

The procedures of Example 1 were repeated to prepare an enzyme electrode having a permselective crosslinked albumin layer and a $H_2O_2$ productive layer in this order on a platinum wire of 2 mm in diameter having a surface which has been polished and cleaned in the same way as in Example 1, except that 5 μl of an aqueous solution containing 2% by weight of the foregoing bovine serum albumin and 0.2% by weight of glutaraldehyde was dropwise applied onto the ground and cleaned surface of the platinum wire, the platinum wire having a coat comprised of said solution thereon was allowed to stand within the saturated vapor atmosphere of glutaraldehyde at 18° C. for 2 hours, and the final heat-treatment of said coat was carried out at 40° C. for 30 minutes.

The resultant enzyme electrode was evaluated by repeating the procedures of Example 1.

The results obtained were as shown in Table 1.

EXAMPLE 3

The procedures of Example 1 were repeated, except that the content of the glutaraldehyde in the aqueous solution for forming the permselective crosslinked albumin layer was increased to an amount of 0.4% by weight, to thereby prepare an enzyme electrode having a permselective crosslinked albumin layer and a $H_2O_2$ productive layer (glucose oxidase containing layer) in this order on a platinum wire of 2 mm in diameter having a surface which has been polished and cleaned in the same way as in Example 1.

The resultant electrode was evaluated by repeating the procedures of Example 1.

The results obtained were as shown in Table 1.

COMPARATIVE EXAMPLE 1

Only the procedures of Example 1 in the case of forming the glucoseoxidase containing layer were repeated to thereby form a $H_2O_2$ productive layer (glucoseoxidase containing layer) on a platinum wire of 2 mm in diameter having a surface which has been polished and cleaned in the same way as in Example 1 to prepare a comparative enzyme electrode.

The resultant enzyme electrode was evaluated by repeating the procedures of Example 1.

The results obtained were as shown in Table 1.

COMPARATIVE EXAMPLE 2

The procedures of Example 1 were repeated to prepare an enzyme electrode having a crosslinked albumin layer and a $H_2O_2$ productive layer (glucoseoxidase containing layer) in this order on a platinum wire of 2 mm in diameter having a surface which has been polished and cleaned in the same way as in Example 1, except that as the aqueous solution for forming the $H_2O_2$ productive layer, there was used an aqueous solution prepared by adding glutaraldehyde in the amount to provide a content of 1.0% by weight in the aqueous solution to a 0.1 mol/l sodim phosphate buffer solution (PH value: 7.0) containing 1% by weight of the foregoing glucose oxidase and 1% by weight of the foregoing bovine serum albumin.

The resultant enzyme electrode was evaluated by repeating the procedures of Example 1.

The results obtained were as shown in Table 1.

COMPARATIVE EXAMPLE 3

The procedures of Example 1 were repeated, except that the content of the glutaraldehyde in the aqueous solution for forming the permselective crosslinked albumin layer was increased to the amount of 0.7% by weight, to thereby prepare an enzyme electrode having a crosslinked albumin layer and a $H_2O_2$ productive layer (glucose oxidase containing layer) in this order on a platinum wire of 2 mm in diameter having a surface which has been polished and cleaned in the same way as in Example 1.

The resultant enzyme electrode was evaluated by repeating the procedures of Example 1.

The results obtained were as shown in Table 1.

TABLE 1

| Example Comparative Example | Sample material to be observed | | |
|---|---|---|---|
| | $H_2O_2$ | Glucose | Ascorbic acid |
| Example 1 | 0.80 μA | 0.20 μA | less than 0.01 μA |
| Example 2 | 0.82 μA | 0.21 μA | 0.03 μA |
| Example 3 | 0.81 μA | 0.19 μA | less than 0.01 μA |
| Comparative Example 1 | 0.81 μA | 0.20 μA | 0.48 μA |
| Comparative Example 2 | 0.80 μA | 0.17 μA | 0.23 μA |
| Comparative Example 3 | 0.70 μA | 0.21 μA | 0.10 μA |

NOTE: Each figure in Table 1 shows the response sensitivity against the sample material.

REMARKS

In Example 1 wherein the content of glutaraldehyde in the aqueous solution containing bovine serum albumin was controlled to 0.2% by weight and the crosslinking reaction was carried out at 4° C. and also in Example 3 wherein the above content of the glutaraldehyde was controlled to 0.4% by weight and the crosslinking reaction was carried out at 4° C., it has been found that any of the enzyme electrodes as obtained exhibit a desired response sensitivity only for hydrogen per oxide ($H_2O_2$) and glucose but not for any interfering material such as ascorbic acid.

From these facts, it has been recognized that in any case of Examples 1 and 3, there was formed a desired permselective layer.

As for the case of Example 2 wherein the crosslinking reaction was carried out at 18° C., it has been found that although the selective response sensitivity is relatively low, there was formed a desired permselective crosslinked albumin layer as expected.

On the other hand, in the case of Comparative Example 1 wherein there was not formed a permselective crosslinked albumin layer, it has been found that the response sensitivities against hydrogen peroxide ($H_2O_2$) and glucose are more or less around the same as in the case of Example 1, but there exhibits a significant response sensitivity also against interfering materials such as ascorbic acid, which is corresponding to about 60% of the response sensitivity against hydrogen peroxide ($H_2O_2$).

As for the case of Comparative Example 2 wherein the content of glutaraldehyde in the glucose oxidase containing solution was made to be 1.0% by weight, it has been found that the crosslinked albumin layer is permeated by ascorbic acid from the fact of exhibiting such great response sensitivity against ascorbic acid which is corresponds to about 30% of the response sensitivity against hydrogen peroxide ($H_2O_2$) From this fact, it has been recognized that a large amount of glutaraldehyde is being permeated into the crosslinked albumin layer from the $H_2O_2$ productive layer (glucoseoxidase containing layer) and because of this, the permselective property of the crosslinked albumin layer is being defected. As for the case of Comparative Example 3 wherein the content of glutaraldehyde in the aqueous solution containing the bovine serum albumin was increased to 0.7% by weight, it has been found that there exhibits a great response sensitivity against interfering materials such as ascorbic acid which is corresponding to about 13% of the response sensitivity against hydrogen peroxide ($H_2O_2$) From this fact, it has been recognized that the crosslinked albumin layer is permeated by interferring materials such as ascorbic acid and because of this, the crosslinked albumin layer is not practically applicable.

EXAMPLE 4

There was used a platinum wire of 2 mm in diameter as the electroconductive substrate. Its terminal was polished with an emery paper, and the remaining unpolished surface was coated with a heat-shrink Teflon (product of E.I. du Pont de Nemours & Co., Inc.)

Electrolytic treatment was conducted for the resultant platinum substrate in a 0.1 M sulfuric acid and with an electric potential of +1.4 V for 10 minutes to thereby form a $PtO_x$ layer. There were used the resultant platinum substrate as the working electrode, a rectangular platinum plate of 1 cm in size as the counter electrode and an Ag/AgCl electrode as the reference electrode respectively. Thereafter, the platinum substrate was well washed with water and it was air-dried at 40° C. for 10 minutes. Then, it was immersed in an anhydrous benzene solution containing 10% by weight of γ-aminopropyltriethoxy silane for 10 minutes.

Onto the surface of the platinum wire, 5 μl of an aqueous solution containing 10 mg/ml of the foregoing bovine serum albumin and 0.11% by weight of glutaraldehyde was dropwise applied. The resultant was transfered into an enclosed vessel the inner space of which was filled with saturated vapor of glutaraldehyde generated from an aqueous solution of the glutaraldehyde and it was allowed to stand at 4° C. for 3.5 hours. Thereafter, it was transfered into an incubator and maintained at 40° C. for 30 minutes to thereby remove the remaining excessive moisture and form a permselective crosslinked albumin layer.

Successively, onto the surface of the permselective crosslinked albumin layer, 5 µl of an aqueous solution prepared by adding glutaraldehyde in the amount to provide a content of 0.2% by weight in the aqueous solution to a 0.1 mol/l sodium phosphate buffer solution (PH value: 7.0) containing 1% by weight of glucoseoxidase (product of Sigma Co., Ltd.; Type II, 36000 units/g) and 1% by weight of the foregoing bovine serum albumin was dropwise applied. The resultant was then allowed to stand at 40° C. for 30 minutes to thereby form a $H_2O_2$ productive layer (glucoseoxidase containing layer).

The thus prepared enzyme electrode was examined in the following way.

That is, after being washed with 0.1 M sodium phosphate buffer solution (PH value: 7.0), the resultant enzyme electrode was set into the three-electrode type cell having a platinum counter electrode and Ag/AgCl reference electrode in a 0.1 M phosphate buffer solution (PH value: 7.0). Then, a voltage of +0.6 V was applied to the enzyme electrode, and glucose in the amount to be a 0.1mM solution was introduced into the system while stirring the buffer solution with a stirrer. The equilibrium output value at that time was recorded.

Then, after the buffer solution was replaced by new one, ascorbic acid in the amount of 0.1 mM in the buffer solution was introduced into the system, and the equilibrium output value was recorded in the same way as the above.

The enzyme electrode used in the above was taken out and placed into a vessel containing a 0.1 M phosphate buffer solution and subjected to ultrasonic treatment at 600 W for 15 minutes. Using the thus treated enzyme electrode, the foregoing measurements were repeated.

Further there were prepared 10 enzyme electrodes by repeating the above procedures. These ten enzyme electrodes were evaluated by repeating the above evaluation procedures. The arithmetical mean value of the resultant output values and the relative standard deviation (±CV%) for the resultant output values before and after the ultrasonic treatment were calculated, and the results and shown in Table 2.

EXAMPLE 5

The procedures of Example 4 were repeated, except that the electrolytic treatment and the silane coupling reagent treatment were omitted, to thereby prepare an enzyme electrode having a permselective crosslinked albumin layer and a $H_2O_2$ productive layer (glucoseoxidase containing layer).

The evaluation procedures of Example 4 were repeated to evaluate the resultant enzyme electrode.

The results obtained are as shown in Table 2.

COMPARATIVE EXAMPLE 4

The procedures of Example 4 were repeated, except that neither the electrolytic treatment nor the silane coupling reagent treatment for the platinum wire were conducted and the aqueous solution for forming the permselecticve crosslinked albumin layer was replaced by an aqueous solution containing 10 mg/ml of the foregoing bovine serum albumin and 0.02% by weight of glutaraldehyde, to thereby prepare an enzyme electrode having a crosslinked albumin layer and a $H_2O_2$ productive layer (glucoseoxidase containing layer).

The evaluation procedures of Example 4 were repeated to evaluate the resultant enzyme electrode.

The results obtained are as shown in Table 2.

TABLE 2

|  | Before supersonic treatment | | After supersonic treatment | |
|---|---|---|---|---|
|  | Glucose | Ascorbic acid | Glucose | Ascorbic acid |
| Example 4 | 0.51 µA (±4.8%) | 0.02 µA (±6.0%) | 0.50 µA (±4.6%) | 0.02 µA (±5.5%) |
| Example 5 | 0.48 µA (±7.0%) | 0.03 µA (±8.2%) | 0.29 µA (±22%) | 0.38 µA (6.5%) |
| Comparative Example 4 | 0.55 µA (±12.0%) | 0.06 µA (±10.1%) | 0.02 µA (±50.6%) | 0.75 µA (±62.0%) |

Note: The figure in the parenthesis shows a relative standard deviation (±CV %).

REMARKS

In the case of Example 4 wherein the electrolytic treatment and the silane coupling treatment for the substrate were conducted, it was found that there is not any meaningful difference between the response sensitivity of the resultant enzyme electrode in the case of not having conducted the ultrasonic treatment and that of the resultant enzyme electrode in the case of having conducted the ultrasonic treatment. In the case of Example 5 wherein neither the electrolytic treatment nor the silane coupling treatment were conducted, it has been found that there is a slight reduction in the output value for glucose and there is an increase in the output value for ascorbic adid.

Further, from the results of Examples 4 and 5, it has been found that when both the electrolytic treatment and the silane coupling reagent treatment are conducted (Example 4), the constituent layers of an enzyme electrode may be effectively prevented from being peeled off at the time of the ultrasonic treatment and there may be prepared a desired stable enzyme electrode of which the permselective crosslinked albumin layer is firmly fixed to the platinum substrate and which excels in durability.

In Comparative Example 4 wherein the content of glutaraldehyde in the bovine serum albumin aqueous solution was made not 0.11% by weight (Example 4) but 0.02% by weight, it has been found that the constituent layer of the enzyme electrode is entirely damaged upon the ultrasonic treatment and because of this, there cannot be obtained such a practically applicable enzyme electrode which can be repeatedly used for a long period of time.

EXAMPLE 6

The procedures of Example 1 in the case of forming the permselective crosslinked albumin layer were repeated to thereby form a permselective crosslinked albumin layer on the polished and cleaned surface of the same kind of the platinum wire as in Example 1.

Successively, onto the surface of the permselective crosslinked albumin layer, 10 μl of an aqueous solution prepared by adding glutaraldehyde in the amount to provide a content of 0.2% by weight in the aqueous solution to a 0.1 mol/l sodium phosphate buffer solution (PH value: 7.0) containing 10 mg/ml of galactoseoxidase (product of Sigma Co., Ltd.; Type V originated in *Doctylium dendroides*,100 units/mg solid) and 5 mg/ml of bovine serum albumin (product of Sigma Co., Ltd.) was dropwise applied and spread on the surface of said albumin layer. The resultant was allowed to stand at 40° C. for 10 minutes, then it was washed with 0.1 mol/l sodium phosphate buffer solution (PH value: 7.0) and air-dried to thereby form an electrode having a permselective crosslinked albumin layer and a $H_2O_2$ productive layer (galactoseoxidase containing layer).

The resultant enzyme electrode was set into the cell of a known flow injection apparatus and the electric potential to the counter electrode was adjusted to $+0.6$ V using potentiostat. Then, a phosphate buffer solution of PH 7.0 was allowed to flow at a flow rate of 1.0 ml/min., and at the same time, an amount of 10 μl for each of 20 mM galactose aqueous solution and 20 mM ascorbic acid aqueous solution was injected to the flow to measure the peak current value for each of the two materials.

As a result, it was found that the enzyme electrode exhibited a response sensitivity of 0.25 μA against galactose and a response sensitivity of 0.016 μA against ascorbic acid.

From these facts, it has been recognized that the enzyme electrode has an excellent permselective property and it is practically applicable.

What is claimed is:

1. A process for preparing an enzyme electrode consisting essentially of the steps of:
    (a) applying an albumin solution containing 0.05 to 0.5% by weight of a multifunctional aldehyde onto the surface of an electroconductive substrate to form a coat comprised of said solution,
    (b) maintaining the atmospheric temperature of 0° C. to 20° C. to thereby form a permselective crosslinked albumin layer, and
    (c) applying a solution containing a hydrogen peroxide productive oxidase and greater than 0 up to 0.5% by weight of a multifunctional aldehyde onto the surface of the above permselective crosslinked albumin layer to form a hydrogen peroxide productive oxidase containing layer thereon.

2. The process according to claim 1, wherein the albumin solution in the step (a) contains 0.1 to 0.5% by weight of a multifunctional aldehyde.

3. The process of claim 1, wherein the step (b) is carried out at a temperature of 0 to 10° C.

4. The process according to claim 1, wherein the electroconductive substrate is platinum.

5. The process according to claim 4, wherein the platinum substrate has a surface treated with a silane coupling reagent.

6. The process according to claim 5, wherein the silane coupling reagent is one or more members selected from the group consisting of γ-aminopropyltriethoxy silane, 4-aminobutyldimethylmethoxy silane and 4-aminobutyltriethoxy silane.

7. The process according to claim 5, wherein prior to subjecting to the silane coupling reagent treatment, the platinum substrate is subjected to electrolytic treatment using the platinum substrate as the working electrode at an electric potential of $+1.0$ to $+1.5$ V vs Ag/AgCl electrode for a period of more than 30 seconds.

8. The process according to claim 1, wherein the multifunctional aldehyde is glutaraldehyde.

9. The process according to claim 1, wherein the albumin is bovine serum albumin.

10. The process according to claim 1, wherein the step (b) is carried out at a temperature of 0 to 10° C. for a period of 20 minutes to 24 hours.

11. The process according to claim 10, wherein the period is 30 minutes to 4 hours.

12. The process according to claim 1, wherein the hydrogen peroxide productive oxidase is selected from glucoseoxidase and galactoseoxidase.

13. The process according to claim 1, wherein the solution in the step (c) further contains a protein other than an enzyme.

14. The process according to claim 13, wherein the protein is albumin.

15. An enzyme electrode produced in accordance with the process according to claim 1.

* * * * *